United States Patent [19]

Holtkamp

[11] Plant 4,208

[45] Feb. 7, 1978

[54] AFRICAN VIOLET PLANT

[76] Inventor: Reinhold Holtkamp, Wertherstrasse 112, 4294 Isselburg, Germany

[21] Appl. No.: 766,580

[22] Filed: Feb. 8, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet plant characterized by upright and strong flower stems bearing non-dropping, violet blooms above the leaves.

1 Drawing Figure

1

The present invention comprises a new and distinct cultivar of African violet plant, botanically known as *Saintpaulia ionantha,* and hereinafter referred to by the cultivar name Florida.

Florida is a product of a planned breeding program which had the objective of creating a new African violet cultivar with large, generally violet flowers, upright and strong flower stems, uniform bouquet, prolonged blooming period with non-dropping flowers, and vigorous growth. These traits in combination were not present in previously available commercial cultivars.

The new cultivar was originated from a cross made by me in a controlled breeding program in Isselburg, Rhineland, Germany. The female, or seed parent was XIX 4256 violet blue, an unpatented cultivar having a color between 1-14 and 1-15 (Horticultural Color Chart of Wilson Colour, Ltd.). The male, or pollen parent was XIX 4158 dark red, also unpatented, color 44-14.

The new cultivar Florida was discovered and selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Florida which in combination distinguish this African violet as a new and distinct cultivar:

1. Strong, upright flower stems.
2. Fast and vigorous growth.
3. Compact and very floriferous flower bouquet, and uniform blooming.
4. Long blooming period.
5. Non-dropping flowers.

The accompanying photographic drawing shows a typical specimen plant of the new cultivar. The colors appearing in the photograph are as true as possible with color illustrations of this type.

In the following description, color references are made to the Horticultural color chart issued by Wilson

2

Colour Ltd., except where general color terms of ordinary significance are obvious.

Botanical classification: *Saintpaulia ionantha,* Ramat. cv. Florida.

Parentage:

*Male parent.*—XIX 4158 dark red.

*Female parent.*—XIS 4256 violet blue.

Propagation: The new cultivar holds its distinguishing characteristics through successive propagations by leaf cuttings and by division of shoots.

Plant:

*Size.*—From 8 cm. to 10 cm. tall when grown in pots, and approximately 22 cm. in diameter when fully grown.

*Leaves.*—General Form: Round to oval (heart-shaped). Diameter: 55–60 mm. Texture: Soft. Aspect: Velvety and hairy. Veins: From underside, well pronounced. Color (upperside): Young leaves 21-15, old leaves 18-15. Color (underside): Grey-green, with parts reddish. Petiole: Green to reddish on young leaves; old leaves on underside between 44-14 and 44-15.

*Flowers.*—Buds: Globular, approximately 7-9 mm. before opening. Sepals: Color: Brown. Calyx: Funnel-shaped, synsepalous. Aspect: Hairy outside. Peduncle: Brown-green.

*Individual flowers.*—Size: 40–45 mm. in diameter. Color: Upperside: 47–9. Underside: 46–5. Borne: Profusely in a central flower head. Shape: 5 petals, 2 small, 3 larger, almost flat. Arrangement: Strong and upright peduncles forming a compact flowerhead. Flowering time: Depending on temperature and light conditions, approximately 3–5 weeks from visible bud to flower.

*Reproductive organs.*—Stamens: Two cells and two anthers. Anthers: Color 26–6. Arrangement: basifixed. Filaments: 4 mm. long, color 26-2. Styles: Color 46-9 on upper. Pollen color: 26-1. Roots: Well developed root system. Disease resistance: Good, as experienced to date. General observations: This plant is a vigorous grower and comes uniformly in bloom. Approximately 5–6 weeks after potting the cultivar shows the first flowers and a bouquet of flower stems with 5–8 flowers. 40–45 mm. in diameter. The flowers do not drop from the stems after withering thereby avoiding damage due to botrytis from fallen blossoms. Diameter of the open flowerhead is 12–15 cm. The foliage tends to spread radially outward from the flower at the center of the plant, with the flowers being free above the leaves.

I claim:

1. A new and distinct cultivar of African violet plant known by the cultivar name Florida and particularly characterized as to uniqueness by the combined characteristics of compact and floriferous flower bouquet, with the flower being supported on strong, upright flower stems; fast and vigorous growth; uniform blooming; non-dropping flowers, and the bouquet being above the leaves which spread radially outward from the center of the plant.

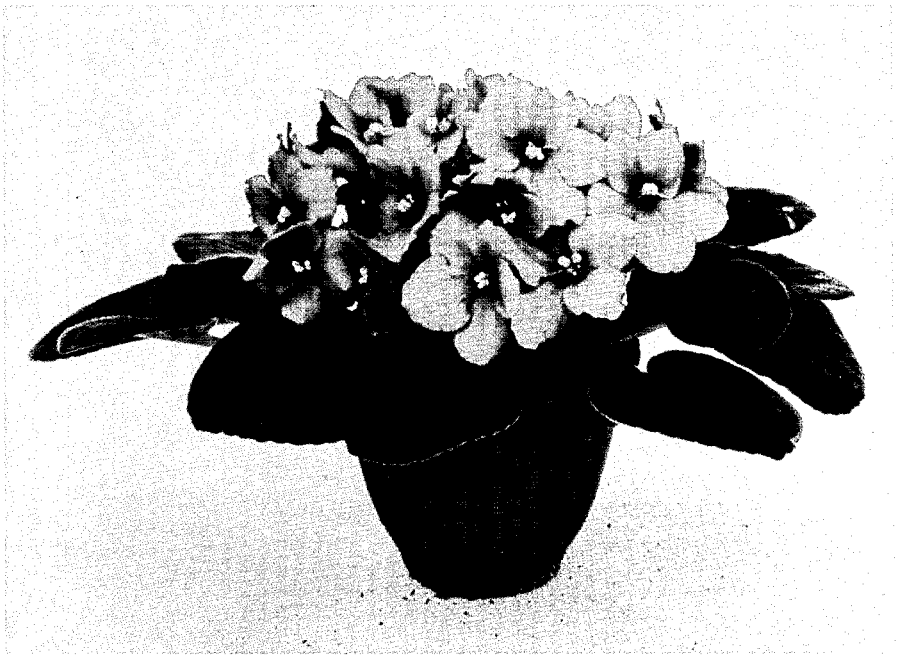

* * * * *